(12) United States Patent
Weling et al.

(10) Patent No.: US 10,466,149 B2
(45) Date of Patent: Nov. 5, 2019

(54) CHEMICAL SENSING DEVICE

(71) Applicant: Triton Systems, Inc., Chelmsford, MA (US)

(72) Inventors: Aniruddha Weling, Framingham, MA (US); Tyson Lawrence, Cambridge, MA (US); Ken Mahmud, Sudbury, MA (US); James Burgess, Ringgold, GA (US); Leonid Krasnobaev, Framingham, MA (US); Joerg Lahann, Ann Arbor, MI (US)

( * ) Notice: Subject to any disclaimer, the term of this patent is extended or adjusted under 35 U.S.C. 154(b) by 0 days.

(21) Appl. No.: 14/452,398

(22) Filed: Aug. 5, 2014

(65) Prior Publication Data

US 2015/0323430 A1 Nov. 12, 2015

Related U.S. Application Data

(60) Provisional application No. 61/862,250, filed on Aug. 5, 2013.

(51) Int. Cl.
| | | |
|---|---|---|
| *G01N 1/40* | (2006.01) | |
| *G01N 33/00* | (2006.01) | |
| *G01N 1/00* | (2006.01) | |
| *G01N 1/44* | (2006.01) | |

(52) U.S. Cl.
CPC ......... *G01N 1/405* (2013.01); *G01N 33/0057* (2013.01); *G01N 1/44* (2013.01); *Y10T 436/173076* (2015.01); *Y10T 436/25875* (2015.01)

(58) Field of Classification Search
CPC ........... G01N 1/405; G01N 1/40; G01N 1/28; G01N 1/00; G01N 33/0057; G01N 33/0036; G01N 33/0027; G01N 33/0006; G01N 33/00; Y10T 436/17; Y10T 436/173076
USPC .......................................... 436/111, 106, 110
See application file for complete search history.

(56) References Cited

U.S. PATENT DOCUMENTS

| | | | |
|---|---|---|---|
| 4,718,268 A * | 1/1988 | Reid ..................... | G01V 9/007 73/19.01 |
| 5,469,369 A | 11/1995 | Rose-Pehrsson et al. | |
| 6,171,378 B1 | 1/2001 | Manginell et al. | |
| 6,345,545 B1 * | 2/2002 | Linker .................. | G01N 1/405 73/863.23 |
| 6,902,701 B1 | 6/2005 | Hughes et al. | |
| 7,122,152 B2 | 10/2006 | Lewis et al. | |
| 7,172,730 B2 | 2/2007 | Carpenter | |
| 7,430,928 B2 | 10/2008 | Grate et al. | |
| 8,117,896 B2 | 2/2012 | Lucas et al. | |
| 8,123,834 B2 | 2/2012 | Masel et al. | |
| 8,511,142 B2 | 8/2013 | Yamazaki et al. | |

(Continued)

OTHER PUBLICATIONS

International Search Report and Written Opinion for PCT/US2014/049820 dated Jun. 25, 2015.

(Continued)

*Primary Examiner* — Christine T Mui
(74) *Attorney, Agent, or Firm* — Pepper Hamilton LLP

(57) ABSTRACT

A chemical sensing system includes a substrate material, a detector capable of indicating a presence of a target compound, gas, or vapor, and a heater for rapidly releasing compounds, gases and vapors from the substrate material. The substrate material acts to concentrate the compounds, gases, and vapors from a sample area for improved detection by the detector.

34 Claims, 13 Drawing Sheets

(56) References Cited

U.S. PATENT DOCUMENTS

| | | |
|---|---|---|
| 8,652,853 B2 | 2/2014 | Markowitz et al. |
| 2006/0021939 A1 | 2/2006 | Mallet et al. |
| 2007/0180933 A1* | 8/2007 | Grate .................. G01N 1/2214 73/863.12 |
| 2008/0150556 A1 | 6/2008 | Han et al. |
| 2009/0223310 A1* | 9/2009 | Syage .................. G01N 1/2205 73/863.12 |
| 2012/0090285 A1 | 4/2012 | Beyer et al. |
| 2012/0137792 A1* | 6/2012 | Bunker ................. B08B 7/0092 73/863.22 |
| 2012/0252129 A1* | 10/2012 | Fu ........................... B01J 20/22 436/128 |
| 2013/0171687 A1 | 7/2013 | Moularat et al. |

OTHER PUBLICATIONS

International Search Report and Written Opinion for PCT/US2014/049809 dated Jun. 25, 2015.

Camara et al., "A Micro Gas Preconcentrator with Improved Performances for Environmental Monitoring," IEEE 2009 International Solid-State Sensors, Actuators, and Microsystems Conference, Denver CO, Jun. 21-25, 2009, 983-986.

Supplementary European Search Report for EP 14859494 dated Feb. 13, 2017.

* cited by examiner

CHEMICAL SENSING DEVICE

CROSS REFERENCE TO RELATED APPLICATIONS

This application claims priority to U.S. Provisional Application No. 61/862,250 filed on Aug. 5, 2013, which is hereby incorporated by reference in its entirety.

GOVERNMENT INTEREST

This invention was made with Government support under Contract No. W911S6-10-C-0011 awarded by the U.S. Army. This invention was also made with Government support under Contract No. D11PC20126 awarded by the U.S. Department of the Interior, NBC Acquisition Services Directorate. The Government has certain rights in this invention.

SUMMARY

The ability to detect trace amounts of volatile organic compounds is often required for chemical sensors such as warfare gas stimulants, explosives, and volatile organic compounds in mouth breath, etc.

Embodiments are directed to preconcentrators including a cartridge having a hollow body sized to contain a substrate enclosed within the cartridge. In some embodiments, the substrate may be metal fiber, woven metal fibers, non-woven metal fibers, porous metal, sheet metal, metal coated glass, metal coated plastic, metal coated ceramic, carbonaceous material, graphite, charcoal, activated carbon, activated carbon cloth, and combinations thereof. In certain embodiments, the substrate may have resistivity of about $10^5$ ohm-meters ($\Omega \cdot m$) to about $10^{-7}$ $\Omega \cdot m$, magnetic permeability of greater than about $1 \times 10^{-4}$ H/m, relative permeability of greater than 100, or combinations thereof. In particular embodiments, the substrate may have an electrical resistivity of greater than $10^3$ $\Omega \cdot m$. In certain embodiments, the cartridge may include at least a first reversibly sealable opening on one side of the cartridge and at least a second reversibly sealable opening on the opposite side of the cartridge.

Other embodiments are directed to a method for detecting an chemical including the steps of collecting particles, gases, and vapors in a preconcentrator having a substrate having resistivity of about $10^5$ ohm-meters $\Omega \cdot m$) to about $10^{-7}$ $\Omega \cdot m$; heating the substrate to release the particles, gases, and vapors; and detecting the chemical in the particles, gases, and vapors. In some embodiments, the substrate may have magnetic permeability of greater than about $1 \times 10^{-4}$ H/m, relative permeability of greater than 100, or combinations thereof. In certain embodiments, the heating may be inductive heating, and in some embodiments, inductive heating is carried out at a frequency of about 100 kHz to about 10 MHz. In particular embodiments, heating may be carried out to about 120° C. to about 300° C.

Further embodiments are directed to a sample collector including a sample collector housing having a preconcentrator holder sized to reversibly receive a preconcentrator; and an air suction pump operably connected to the sample collector housing and configured to produce air flow through the preconcentrator. In some embodiments, the sample collector may further include a pulsed air nozzle connected to the sample collector housing, and in certain embodiments, an air compressor may be operably connected to the sample collector housing and configured to expel air from the pulsed air nozzle and direct the expelled air toward a sample collection area. In various embodiments, the air suction pump may provide a flow of 1 m³/min to 10 m³/min. In certain embodiments, the preconcentrator may include a substrate having resistivity of about $10^5$ ohm-meters ($\Omega \cdot m$) to about $10^{-7}$ $\Omega \cdot m$ Additional embodiments are directed to a system including a sample collector having a sample collector housing having a preconcentrator holder sized to reversibly receive a preconcentrator; and a detector including a detector housing having an detector access port sized to reversibly receive the preconcentrator; an induction heater contained within the detector housing, the induction heater configured to heat the preconcentrator; and a sensing system operably connected to the access port and positioned to receive particles, gases, and vapors from the preconcentrator when the preconcentrator is received by the detector. In some embodiments, the detector my further include an air suction pump operably connected to the access port and configured to produce air flow through the preconcentrator, and in some embodiments, the air suction pump may provide a flow of 1 m³/min to 10 m³/min. In certain embodiments, the preconcentrator may include a substrate having resistivity of about $10^5$ ohm-meters ($\Omega \cdot m$) to about $10^{-7}$ $\Omega \cdot m$. In various embodiments, the preconcentrator may include a cartridge and a substrate having a resistivity of about $10^5$ ohm-meters ($\Omega \cdot m$) to about $10^{-7}$ $\Omega \cdot m$ enclosed within the cartridge. in some embodiments, the detector may include a temperature feedback that limits the temperature to about 120° C. to about 300° C. In particular embodiments, the detector further comprises a compressor operably connected to the detector access port and configured to generate a differential pressure across the preconcentrator when the preconcentrator is received by the detector.

DETAILED DESCRIPTION

Figure 1:
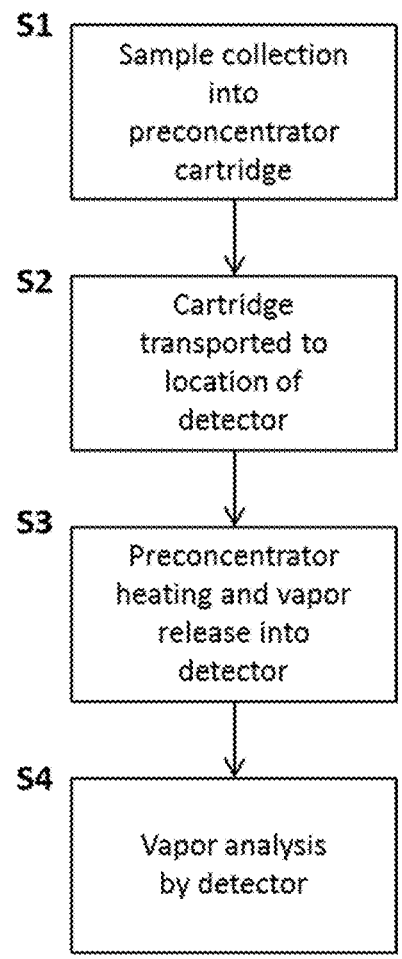
FIG. 1 represents a general flow diagram of operating a sensing system according to an embodiment.

Embodiments of the invention are directed to systems and methods for chemical detecting and various components of the systems. Some embodiments are directed to preconcentrators and the various components of a preconcentrator collector system for collecting and concentrating chemicals from a collection area. Other embodiments are directed to devices including sensors and other components capable of releasing the chemicals collected from the collection area and sensing particular chemicals from the collected sample. Still other embodiments using the preconcentrators, sample collectors, and sensors, detectors and other devices associated with these systems.

In various embodiments, the preconcentrator may be a hollow body sized to contain a substrate capable of reversably bonding to various chemical species. The tubular hollow body may have at least a first reversibly sealable opening on one side of the hollow body and at least a second reversibly sealable opening on the opposite side of the hollow body. For example, in some embodiments, the preconcentrator may be cylindrical cartridge with circular openings on each end of the cylinder. In other embodiments, the preconcentrator may be disk shaped having concave disk shaped ends connected by a broad cylindrical body providing a substantially obround hollow body. Openings may be provided on any surface of the disk shaped body.

The reversible sealable openings on the preconcentrator may be created by any means. For example, in certain embodiments, the reversible seal may be removable caps, stoppers, corks, plastic films, or combinations thereof. In other embodiments, the reversible seals may be integral to the cartridge. For example, the openings may be sealed using hinged covers or slide covers that can be moved to allow access to the internal hollow body of the cartridge during use and then resealed after the sample has been obtained. In still other embodiments, the openings may be sealed using both integral hinged or slide covers and removable caps or plastic films.

Certain embodiments are directed to preconcentrators having a substrate that is capable of reversably bonding to various chemical species, and in certain embodiments, the substrate may be capable of releasing bound chemical species when heated or placed in a magnetic field. In some embodiments, the substrate may a resistivity of about $10^3$ ohm-meters ($\Omega \cdot m$) to about $10^{-9}\ \Omega \cdot m$, about $10^5$ ohm-meters ($\Omega \cdot m$) to about $10^{-7}\ \Omega \cdot m$, about $10^4$ ohm-meters ($\Omega \cdot m$) to about $10^{-6}\ \Omega \cdot m$, about $10^3$ ohm-meters ($\Omega \cdot m$) to about $10^{-5}\ \Omega \cdot m$, or any range or individual value encompassed by these example ranges. In some embodiments, the substrate may have a magnetic permeability ($\mu$) of greater than about $1 \times 10^{-4}$ H/m or, in certain embodiments, about $1 \times 10^{-5}$ H/m to about about 10 H/m, about $1 \times 10^{-4}$ H/m to about 1 H/m, about $1 \times 10^{-3}$ H/m to about 0.1 H/m, or any range or individual value encompassed by these example ranges. In some embodiments, the substrate may have a relative permeability of greater than 100, or, in particular embodiments, the relative permeability may be about 75 to about 500, about 100 to about 400, about 150 to about 250 or any range or individual value encompassed by these example ranges. Of course, in various embodiments, the substrate may have any combination of resistivity, magnetic permeability, and relative permeability in which each range is encompassed by one or more of the example ranges described above. The substrate of such embodiments may be composed of a variety of materials including, for example, metal fiber, woven metal fibers, non-woven metal fibers, porous metal, sheet metal, metal coated glass, metal coated plastic, metal coated ceramic, carbonaceous material, graphite, charcoal, activated carbon, activated carbon cloth, and combinations thereof. In some embodiments, the substrate may be porous to enable the flow of air through the preconcentrator.

Examples of substrates may include, but are not limited to, steel wool, nickel foam, $ZnFe_2O_4$ nanorods, iron nanoparticles/glass wool, Co-ferrite aerogel, magnetic stainless steel wool and the like. The physical properties of these substrates are described in Table 1.

TABLE 1

| Substrate material | $\mu$ (H/m) | Specific Heat (kg/kJ ° K) | Surface Area (m$^2$/g) | Heating Rates (° C./s) | Pressure Drop (PSI) |
|---|---|---|---|---|---|
| Steel Wool (#3) | 8.75E−4 | 0.49 | 0.0075 | 50 | |
| Steel Wool (#0000) | 8.75E−4 | 0.49 | 0.0759 | 76 | 0.38 |
| Nickel Foam | 1.25E−4 | 0.54 | 0.0026 | 60 | 0.08 |
| $ZnFe_2O_4$ Nanorods | 4.01E−4 | — | 13.6 | — | |
| COTS Ferrite rod (NiZn) | 5.03E−5 | 1.05 | 0.000949 | 45.4 | 0.79 |
| Iron Nanoparticles/ Glass Wool | ~1 | 0.67 | 0.7 | 17.5 | |
| Co-Ferrite aerogel* | 3.27E−4 | — | 350 | — | 1.39 |
| 434 Magnetic Stainless Steel wool (#3) | 8.75E−4 | 0.49 | 0.0075 | 52 | 0.37 |

In Table 1, magnetic permeability ($\mu$) defines the response of material to magnetic field, specific heat defines the material's ability to be heated, surface area describes the exposed surface area of the material that is capable of binding to a chemical species, where a higher surface area means higher density of surface binding sites, heating rate describes the rate at which the substrate can be heated, and pressure drop describes the maximize air flow required to increase sample volume. In particular embodiments, the substrate may be steel wool.

In some embodiments, the preconcentrator may include a coating on the substrate described herein. The coating in such embodiments may be any coating that improves either bonding of chemical species to the substrate, release of the bound chemical species, or combinations thereof. In certain embodiments, the coating may be an organic coating. In some embodiments, the coating may generally increase the affinity of the substrate for various chemical species. In other embodiments, the coating may be chemically selective allowing the coated substrate to have an increased affinity for a specific target species or a particular class or group of target species. For example, in some embodiments, the coating may provide higher affinity for target chemical species, while reducing the substrates affinity for common background chemicals, such as water vapor, cigarette smoke, exhaust fumes, gasoline fumes, dust, pollen, and the like or combinations thereof. In certain embodiments, the coating may increase the affinity of the substrate for chemical species including, but not limited to, explosives, chemical warfare agents, and toxic industrial compounds.

In particular embodiments, the coating may provide discrimination between water and polar analytes. Thus, the coating may have an affinity for polar chemical species while repulsing water and non-polar chemical species, such as water vapor, cigarette smoke, exhaust fumes, gasoline fumes, dust, pollen, and the like or combinations thereof. In some embodiments, this discrimination can be achieved by combining polar and non-polar functional groups into the coating, and in other embodiments, different coating materials having polar or non-polar functionality can be combined and coated onto the substrate. Including both polar and non-polar functionality in the coating may allow the non-polar portion to reject water and non-polar interferents, while the polar portion adsorbs the polar chemical species. In this manner, the spurious signals due to water and interferents can be eliminated, while simultaneously enhancing the signals due to the polar molecules. Embodiments, are not limited to particular polar or non-polar functional groups. For example, in some embodiments, the polar functional groups may include amide (—C(O)NH$_2$), C$_1$-C$_{10}$ alkyl amide, carboxylic acid (—COOH), C$_1$-C$_{10}$ alkyl carboxylic acid, hydroxyl (—OH), C$_1$-C$_{10}$ alkyl hydroxyl, C$_1$-C$_{10}$ alkyoxy, aldehyde (—C(O)H), C$_1$-C$_{10}$ alkyl aldehyde, ketone (—C(O)CH$_3$), C$_1$-C$_{10}$ alkyl ketone, amine (—NH$_2$), C$_1$-C$_{10}$ alkyl amine, epoxide, carbonyl group, and combinations thereof. In various embodiments, the non-polar functional groups incorporated into the coatings described above may be C$_1$-C$_{10}$ alkyl, C$_2$-C$_{10}$ alkene, C$_2$-C$_{10}$ alkyne, C$_6$-C$_{16}$ arene, halide (Br, F, Cl), C$_1$-C$_{10}$ alkyl halide, cycloalkyl, and combinations thereof.

In certain embodiments, the coatings may be a polymer having aromatic, or aliphatic backbone, and in certain embodiments, the backbone may contain benzene, toluene, xylene, cyclohexane, dimethylcyclohexane, ethylcyclohexane, and combinations thereof. In particular embodiments, the coating may be composed of functionalized xylene. For example, the coating may be a copolymer of 4-hydroxy[2.2]paracyclophane and 4-perfluoroalkyl-carbonly[2.2]paracyclophane, in which the —OH groups on the surface allow for the attachment of polar molecules while the Teflon-like fluorine chain acts as a hydrophobic barrier to water stabilization on the surface.

The coatings of various embodiments are generally thinly applied to the substrate. For example, in certain embodiments, the coating may have a thickness of about 200 nm. In other embodiments, the coating may have a thickness of about 100 nm to about 500 nm. The coating may be provided on any surface of the substrate, and in certain embodiments, the substrate may be substantially coated on all surfaces. For example, the coating may cover from about 50% to about 99% of the total surface area of the substrate, or in some embodiments, the coating may cover about 75% to about 98%, about 80% to about 97%, about 85% to about 95% of the total surface area of the substrate or any individual value or range encompassed by these values.

The coating may be applied by any method that provides for a conformal coating over the various features of the substrate. In an embodiment, the coating may be applied by chemical vapor deposition (CVD). Vapor-based coating enables coating a variety of substrate architectures ranging from planar surfaces such as metal and silicon to interwoven scaffolds such as steel wool. Monomers having diverse functionalization, such as, for example, functionalized monomers of highly adhesive p-xylene, may be applied by CVD, and a resultant copolymerization leads to uniform multi-functional surfaces, and also modulates surface properties such as composition, hydrophobicity, and surface charge. This allows for conformal coating of surfaces instead of the spin-coating or wet deposition methods that are common in the field. Conformal coatings are important to micro-machined sensors and pre-concentrators due to gaps that may form in the coating due to surface tension in the spin cast film. In some embodiments, the coating may be applied by other techniques known in the art, such as layer-by-layer assembly, one sided plasma enhanced chemical vapor deposition, and one-sided photopolymerization.

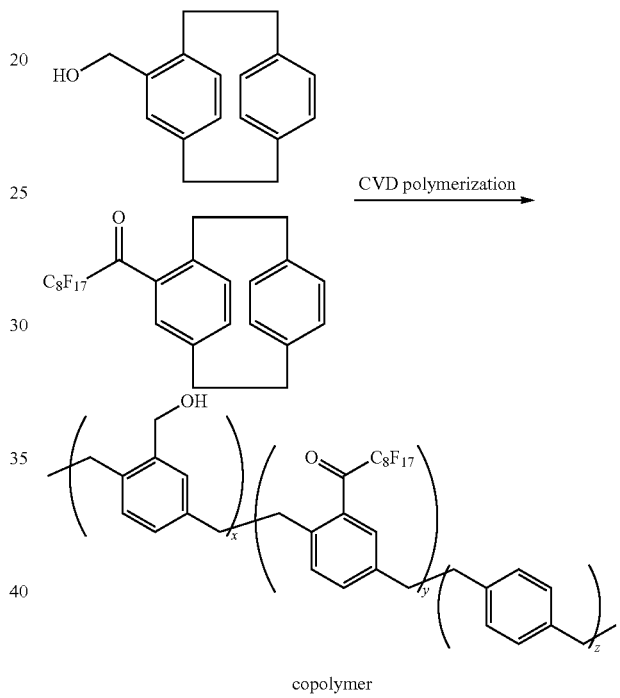

copolymer

The preconcentrators described herein can be used in a variety of systems for sensing chemical species. For example, in some embodiments, the preconcentrators may be incorporated into larger sensing systems. In some embodiments, the sensing systems may include a separate sample collector and detector. FIG. 1 is a flow chart describing example of a process by which a system including separate sample collection followed by detection. In such embodiments, sample collection S1 may be carried out by drawing air into a preconcentrator such as the preconcentrator cartridge described above, and various chemical species and other vapors may become associated with the substrate in the preconcentrator. In some embodiments, after sample collection, the preconcentrator cartridge may be sealed. The preconcentrator cartridge can then be transported S2 to a location that includes a detector. In some embodiments, the preconcentrator cartridge may be taken to the detector directly following sample collection. For example, the preconcentrator may be part of a sample collector and the sample collector may be part of a transportable and movable system that can be carried in a backpack or shoulder carrier, rolled on castors or a mobile cart, or otherwise transported with the user, so that sample collection and transport to the detector can occur simultaneously. In other embodiments, the detector may be maintained at a fixed position and the user may transport preconcentrator to the detector or have the detector transported to the preconcentrator. The preconcentrator may then be heated S3 to release the chemical species and other vapors that were associated with the substrate during sample collection and the chemical species and vapors may be released into the detector. In some embodiments, heating and release into the detector may occur in the detector. For example, the detector may be equipped with an induction heater designed to surround the preconcentrator and means for directing air flow through the preconcentrator and into the detector. In such embodiments, chemical species and vapors may be released from the preconcentrator substrate and simultaneously directed into the detector. In other embodiments, the heating unit may be separate from the detector. The detector may be utilized to detect the chemical species S4 released into the detector.

Figure 4:
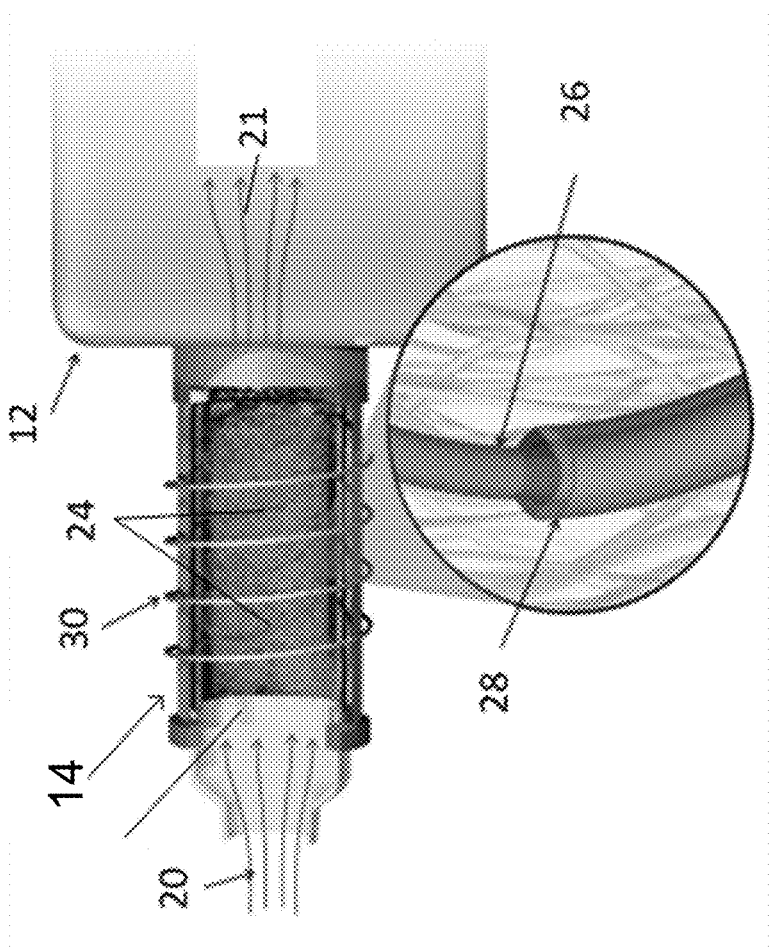
FIG. 4 depicts a chemical sensing system having an induction heater according to an embodiment.

The preconcentrator includes all of the components and physical properties described above. In some embodiments, the preconcentrator may include a hollow cartridge that encapsulates the substrate and may be constructed from various materials such as, for example glass, quartz, Teflon, plastic, aluminum, and the like and combinations thereof. The preconcentrator may include a high surface-area substrate. As shown in the detail of FIG. 4, in some embodiments, the coated substrate may include a porous substrate material 26 with a conformal, stable, chemically selective surface treatment, or coating 28, configured to have an affinity for the target substrate or substrates. In other embodiments, the substrate may be uncoated.

Figure 2:
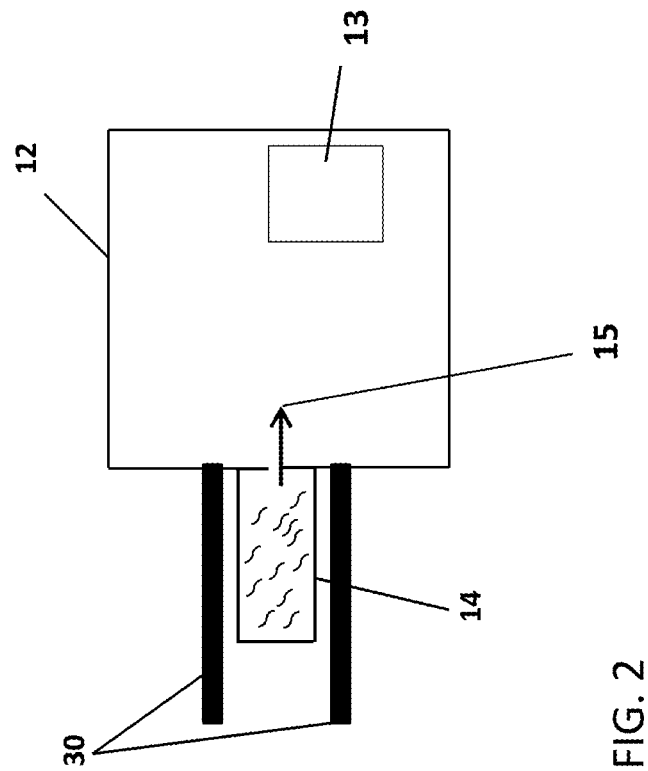
FIG. 2 depicts a general representation of a chemical sensing system according to an embodiment.
Figure 2:
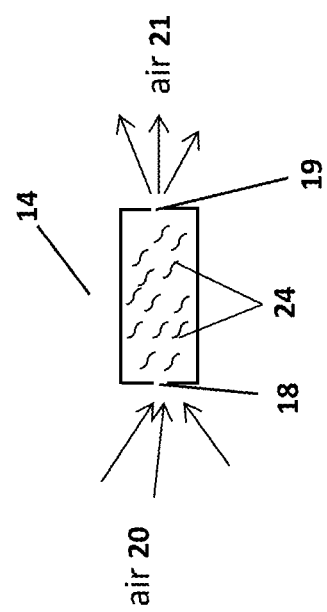

The preconcentrator cartridge in FIG. 2 may include an inlet 18 and outlet 19 that may be reversible sealable openings. The reversible sealable openings on the preconcentrator may be created by any means. For example, in certain embodiments, the reversible seal may be removable caps, stoppers, corks, plastic films, or combinations thereof. In other embodiments, the reversible seals may be integral to the cartridge. For example, the openings may be sealed using hinged covers or slide covers that can be moved to allow access to the internal hollow body of the cartridge during use and then resealed after the sample has been obtained. In still other embodiments, the openings may be sealed using both integral hinged or slide covers and removable caps, plastic films, or stoppers. The stoppers may be constructed of rubber or plastic. To remove the contents of the preconcentrator, the stopper may be pinched with a hypodermic needle.

Figure 3:
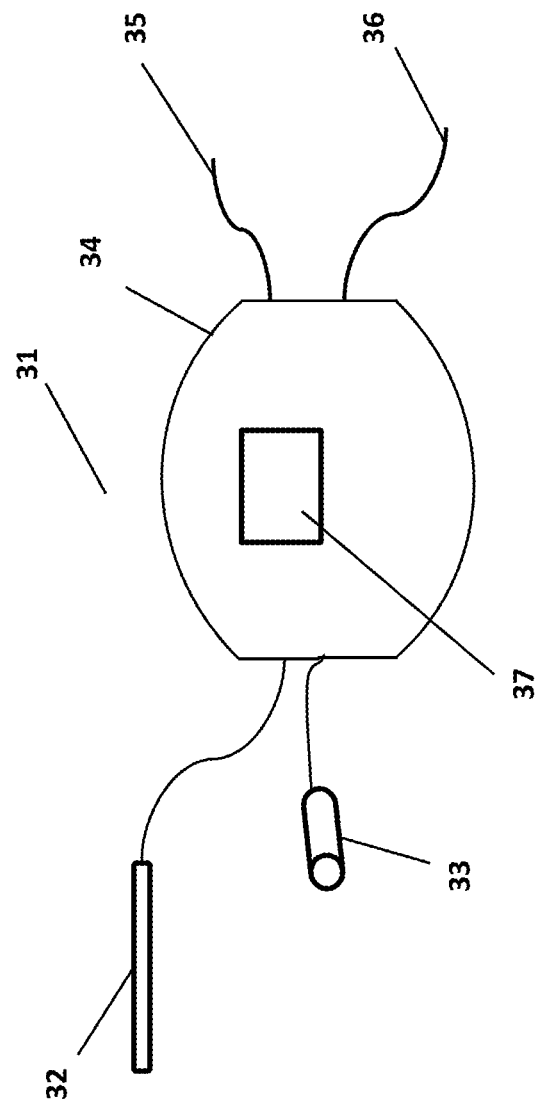
FIG. 3 depicts a sketch of a sample collector according to an embodiment.

Various embodiments include a sample collection system including a sample collector 31 as illustrated in FIG. 3. In some embodiments, the preconcentrator may be reversibly attached to the sample collector, such that a preconcentrator can be inserted into the sample collector, a sample may be collected, and the preconcentrator may be removed from the sample collector and inserted into a detector device. In other embodiments, the preconcentrator may be integrated into the sample collector as part of a larger detector system, and in certain embodiments, this system can be transportable and movable or can be carried in a backpack or shoulder pack.

In various embodiments, the sample collector 31 may include a housing 34. In some embodiments, the housing may include an integrated preconcentrator holder sized to receive the preconcentrator and hold the perconcentrator during sample collecting. The holder may be equipped with one or more reversible fasteners. For example, the preconcentrator or the cartridge may include grooves that reversible interlock with grooves in the preconcentrator holder by twisting or screwing the preconcentrator into the holder. In other embodiments, the preconcentrator or the cartridge may include one or more ridges that interconnect with ridges in the preconcentrator holder allowing the preconcentrator to snap into the preconcentrator holder. In some embodiments, the preconcentrator holder 33 may be attached to the housing body 34 by means of a flexible tubing or a hose allowing the user to move the preconcentrator into small spaces. The preconcentrator holder 33 in such embodiments may be attached to the distal end of the tubing or has and may reversibly hold the preconcentrator 14 during the operation of the preconcentrator using one or more reversible fasteners such as those described above. The preconcentrator holder may further include mechanism for opening the reversibly sealable ends of the preconcentrator or the cartridge such that when the preconcentrator is in place, the opening inside the preconcentrator holder is opened allowing free flow of air from the preconcentrator into the sample collector. In other embodiments, the user may remove the reversibly sealable end of the preconcentrator or the cartridge before introducing the preconcentrator into the preconcentrator holder.

Air may be drawn through the preconcentrator by an air suction pump 36 that is operably connected to the preconcetrator holder 33. The air suction pump 36 may be any type of air pump known in the art including, for example, a diaphragm pump, rotary vane pump, a piston pump, or a fan the produces air current through the preconcentrator holder and preconcentrator. In particular embodiments, the air suction pump may be a regenerative air pump. The flow of the air through the preconcentrator allows the analytes and chemical compounds to be trapped inside the preconcentrator by binding to the coated substrate, and the air flow produced by the air suction pump 36 can vary among embodiments. For example, in some embodiments, the air flow may produce through the preconcentrator may be 1 $m^3$/min to 10 $m^3$/min or any individual value or range encompassed by this range.

In some embodiments, the sample collector may also include a pulsed air nozzle 32 connected to the sample collector housing body 34 that expels air from the sample collector and is positioned to blow air into a sample collection area disturbing particles that may have settled on surfaces in the sample collection area. The pulsed air nozzle may be integral to the sample collection having an outlet that is on a surface of the sample collector, and in some embodiments, the outlet may include moveable blades or a nozzle that directs the flow of air away from the sample collector. In other embodiments, the pulsed air nozzle may include a flexible hose or tubing that allows the flow of air to be directed by the user. In some embodiments, the pulsed air nozzle including a flexible hose or tubing may be mounted on a tripod. An air compressor 35 for producing expelled air can be operably connected to the pulsed air nozzle 32. In some embodiments, a number of pulsed air nozzles and preconcentrator holders may be connected to the same air suction pump and air compressor allowing for multiple simultaneous sample collections.

In particular embodiments, the housing body may include control devices and components 37 to control the working of the air suction pump and the air compressor. In particular embodiments, the sample collector, the air suction pump, and air compressor can be mounted on a compact wheeled cart.

After sample collection, the preconcentrator may be removed from the sample collector, and then the preconcentrator 14 may be reversibly connected to a detector through an access port on the detector device. The detector may include a rapid chemical desorber, that may be configured as a heat source 30. In an embodiment as represented by FIG. 4, the desorber may be configured as a non-contact miniature induction heater 30. In an embodiment, the indication heater may be battery powered for portability of the detection system. Alternatively, for a detection system that may be mounted or placed in a more permanent location, a plug-in power source may be provided, and may include a plug for an alternating current outlet, as well as additional appropriate power conversion components to vary the voltage, amperage, and type of current, etc.

In order to increase the concentration of target chemical compounds in the vapor sample analyzed by a trace detection system, the collected chemical vapor may be released from the substrate in a very short burst to thereby enter the detection device as a more highly concentrated sample. This may be accomplished by a controlled rapid heating of the preconcentrator 14. In an embodiment, the heating may be non-contact inductive heating that raises the temperature of the substrate substantially uniformly to a temperature of about 150° C. to about 250° C. in less than about 5 seconds.

In some embodiments, the detector 12 in FIG. 2 may include a heating element 30 that facilitates release of the bound analytes from the substrate 24. In some embodiments, a compressor may be further attached to the detector that generates a differential pressure across the preconcentrator 14. The differential pressure across the preconcentrator provides flow of vapors released from the preconcentrator substrate 24 and is injected into a chemical analyzer 15. Operation of the heating element 30 may be synchronized with time, when differential pressure across the preconcentrator changes, and air with vapors injected into chemical analyzer. The device has means to control the volume of air with released vapors injected into chemical analyzer. Such control is provided by control of time, when differential pressure across the preconcentrator is not equal to zero.

Figure 5:
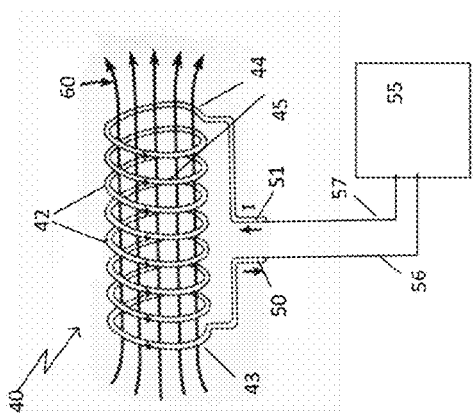
FIG. 5 depicts a general representation of an induction heating system.

As represented in FIG. 5, an induction heater may include an induction coil 40 (also generally represented as 30 in FIG. 4) having a plurality of turns of an electrically conductive material 42, such as, for example a copper wire, that form a tunnel-like structure. While the solenoid-type coil 40 that is shown in FIG. 5 is one illustrative embodiment having about eight individual coil turns, it should be understood that the solenoid-type coil can include any desired number of individual coil turns to form a solenoid-type coil having a desired specified length. The solenoid type coil 40 has opposite open ends 43 and 44, and a hollow portion 45 of a substantially uniform diameter that extends along the entire length of the coil and is adapted to receive the component to be heated, which as shown in FIG. 4, may be a sample collection cartridge 24. The induction heating coil 40 may be provided with terminals 50, 51 to connect the solenoid-type coils to a high frequency power source 55 via power leads 56, 57.

The use of such an induction coil 40 may allow for a rapid and accurate method of uniformly heating the contents of the preconcentrator to a desired and predetermined temperature. As shown in FIG. 4, a method of heating may include providing an induction heating device that includes an elongated solenoid-type induction heating coil 30 in close proximity around the preconcentrator 14. The term "close proximity" is intended to refer to the positioning of the outer surface of the preconcentrator 14 in relation to the induction coil 30. Preferably, the distance between the outer surface of the preconcentrator 14 and the coil 30 should be such that the magnetic field generated by the coil does not melt the preconcentrator, but that the portion of the preconcentrator to be heated is within the magnetic field generated by the coil to maximize the induction heating of that portion of the preconcentrator. As such, an air gap may be present between the outer surface of the portion of the preconcentrator 14 to be heated and the induction coil. The air gap must be such that the induction coil does not contact the preconcentrator. Without limitation, the air gap between the preconcentrator and the induction coil may be about 0.1 to about 0.5 inch.

The induction heating coil may then be provided or energized with a source of high frequency power, such as a radio-frequency power. The power supplied to the induction heating coil may be a supply of alternating current power. The provision of the high frequency alternating current to the induction coil produces an electromagnetic field 60 (as shown in FIG. 5), within the solenoid-type coil 30, 40. The electromagnetic field produces eddy currents in the substrate material 26 and, thus, the coating 28 on the substrate is heated. The high frequency current is provided to the induction coil for a time sufficient to heat the coating material to a desired and predetermined temperature to release any bound analyte. The analyte may then be free to be carried by an airflow 21 into the detector 12.

An induction heater generally may operates at either medium frequency (MF) or radio frequency (R) ranges. The term "R induction" is traditionally used to describe induction generators designed to work in the frequency range from about 100 kHz up to about 10 MHz, in practical terms however the frequency range tends to cover about 100 to about 200 kHz. The output range typically incorporates about 2.5 to about 40 kW. The term "MF induction" is traditionally used to describe induction generators designed to work in the frequency range from about 1 to about 10 kHz. The output range typically incorporates about 50 to about 500 kW. Induction heaters operating within the MF ranges are normally utilized on medium to larger components and applications.

In an embodiment wherein the high surface-area substrate is made out of magnetic stainless steel wool having a high magnetic permeability, an inductive heating may be very efficient with minimal power consumption. In such a scenario, the inductive heating may require less than about 10 watts to heat about 0.1 gram of substrate to the desired temp. With the possibility of such low power requirements, the rapid desorber could be powered by rechargeable batteries, and depending on the battery size and configuration, may allow for over 300 current shots on a single charge. The induction heater circuitry may also include built-in over-current protection and feedback controls to limit peak substrate temperature.

Figure 6:
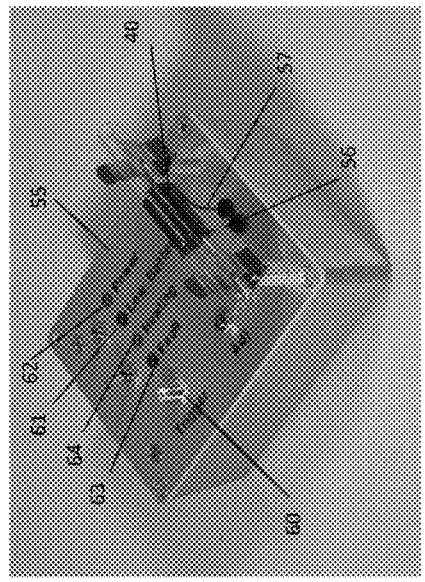
FIG. 6 depicts a miniature trace explosives trace preconcentrator device according to an embodiment.
Figure 7:
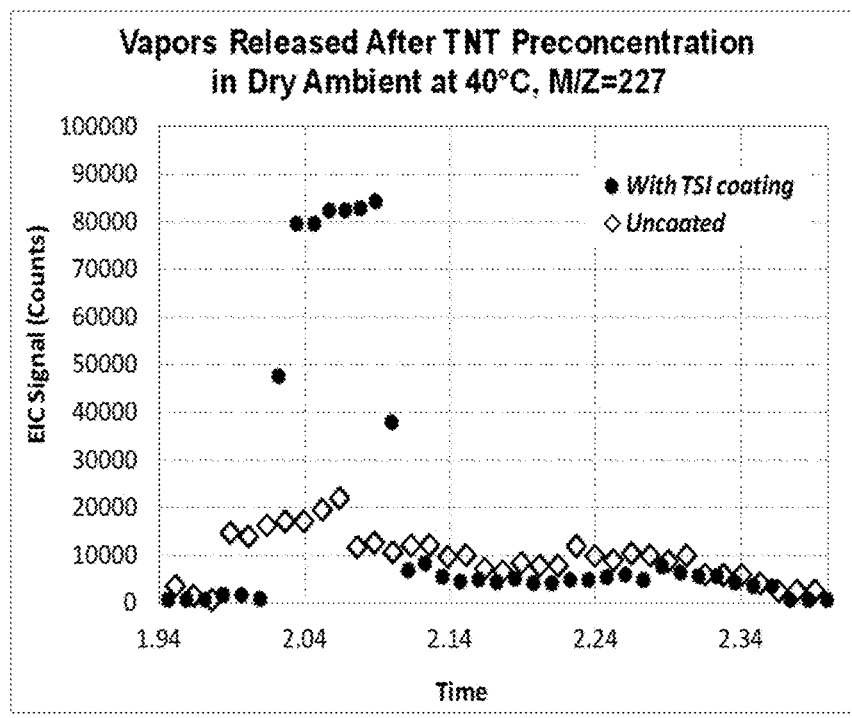
FIG. 7 shows MS data for TNT vapors flash extraction after preconcentration in dry ambient. Initial TNT vapor flow was below detection limit (<1000 counts).
Figure 8:
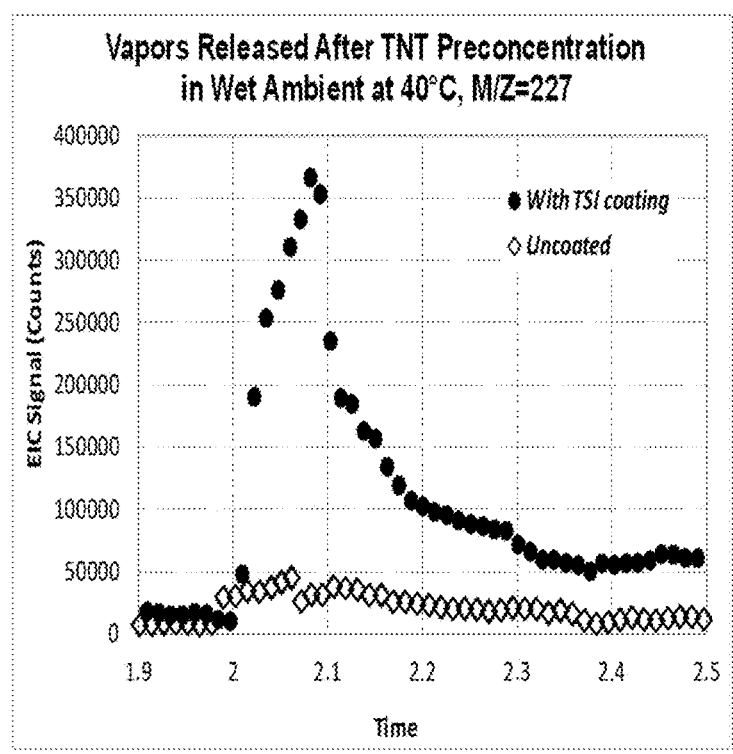
FIG. 8 shows MS data for TNT vapors flash extraction after preconcentration in wet ambient.

Some examples of components of the heater circuitry may include: a basic LC tank circuit driven by MISFIT switches; an on-board tunable frequency generator (100-400 kHz); an on-board power supply (battery); an on-board temperature measurement for temperatures up to about 350° C.; an over-current protection circuit; an over-voltage protection circuit; a temperature feedback to limit temperature to about 250° C.; a self-tuning frequency feedback loop; an activation circuit to synch with external trigger or manual switch 60 in FIG. 6; and on-board status lights, that may include the following as non-limiting examples, a low battery indicator 61, a power-on indicator 62, a fault indicator 63 to indicates over-current or abnormal frequency, and a "Heating" indicator 64. The protection circuits may provide multiple protections against abnormal load conditions, and may include, as non-limiting examples: robust output transistors; a shutdown on fault conditions, such as input current over 4 amps or a frequency that is too high; a "Pecking" with 2 second time-out on continuous fault conditions so that, for example, a fault may be left indefinitely without damage; protection against accidental high coil voltages; and a circuit board such as a printed circuit board (PCB) designed to accommodate high currents.

In an embodiment, a miniature induction heater for the detection system may be powered by a small Lithium-Polymer Battery (11.1V, 325 math), and the coil voltage may be adjustable from about 20Vp-p (Volts peak to peak) to about 100Vp-p. The feedback system may be configured to regulate coil voltage to accommodate changes in coil and sample properties. The heating may be controlled by manual switch or by logic input, and the coil and sample cartridge may be easy to remove and replace when needed.

Induction heating of the pre-concentrating chamber allows for high substrate heating rates, with low power consumption in a low maintenance device. With induction heating fast desorption of the analyte may be achieved as the RF-coil may induce a magnetic field to cause the magnetic substrate to heat rapidly (greater than about ° 80 C/sec), with minimal power usage—low thermal mass and high permeability may use less than about 10 Watts per shot of RF power. An induction heater may also provide reduced maintenance costs as the induction process requires no moving parts or heating meshes/coils that typically require periodic replacement. In addition, reduced usage costs may also be provided since the coated substrates for use in the detection system may be provided as easily replaceable cartridges. And, as a safety feature, the maximum temperature may be controlled by choice of substrate material, mounting geometry, and coating.

The sensing systems and devices described herein can have multiple components, such as one or more preconcentrators, one or more sample collectors, one or more heating elements, and one or more detectors as a part of a single unit. In some embodiments, the sensing systems may include a preconcentrator, a sample collector, a heating element, and a detector as separate units, preferably on movable carts. In other embodiments, the sensing systems may include a preconcentrator and a sample collector as one unit, and a heating element and a detector as part of one unit. In additional embodiments, the sensing systems may include a preconcentrator, a sample collector, and a heating element as part of one unit, and a detector as a separate unit. In further embodiments, the sensing systems described herein may include a preconcentrator, a heating element, and a detector. The present invention is not to be limited in scope by the specific embodiments described above. Many modifications of the present invention, in addition to those specifically recited above would be apparent to those skilled in the art in light of the instant disclosure.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Example

A novel miniature trace explosives trace preconcentrator device was developed as shown in FIG. 6. The device had the following characteristics as shown in Table 2

TABLE 2

| | |
|---|---|
| Collected media | Particles, aerosol and vapors |
| Type of substrate | Proprietary functional monomer on stainless steel wool |
| Pulsed heating | Inductive RF (patent pending) |
| Preconcentration factor | Up to 1000 |
| Low pressure drop | 0.4 PSI for 0.1 g substrate |
| Fast heating | 85-125° C./sec |
| Released vapors volume | As little as 5-10 mL. Could be adjusted. |
| Tuned affinity to a group of chemicals | Nitro-, Phosphorus-, etc. |
| Low price for the coated substrate | <$0.15 |
| Reusable | Up to 20 times |
| Low outgassing | Up to 275° C. |
| Excellent coating adhesion | At least 20 cycles |
| Coating thermal stability | AT least 250° C. |
| Not sensitive to a thermal shock | Tested at 150° C./sec |
| Low mass media | 0.1 g and 0.5 g |
| Low power consumption | <50 Joules for heating 0.1 g substrate to 250° C. |
| COTS detectors tested with pre-concentrator | IMS, DMS and MS |
| Selectivity improvement in presence of | $2^{nd}$ hand smoke, gasoline exhaust |
| Device Size | 3.2" × 1.7" × 4.3" |
| Pre-concentrator tube ID | 0.2" |
| Weight with a battery | 312 g (11 oz) |
| Battery | Lithium-Polymer Battery (11.1 V, 325 mAh) |
| Number of heating cycles on a battery | Up to 200 |

Figure 9:
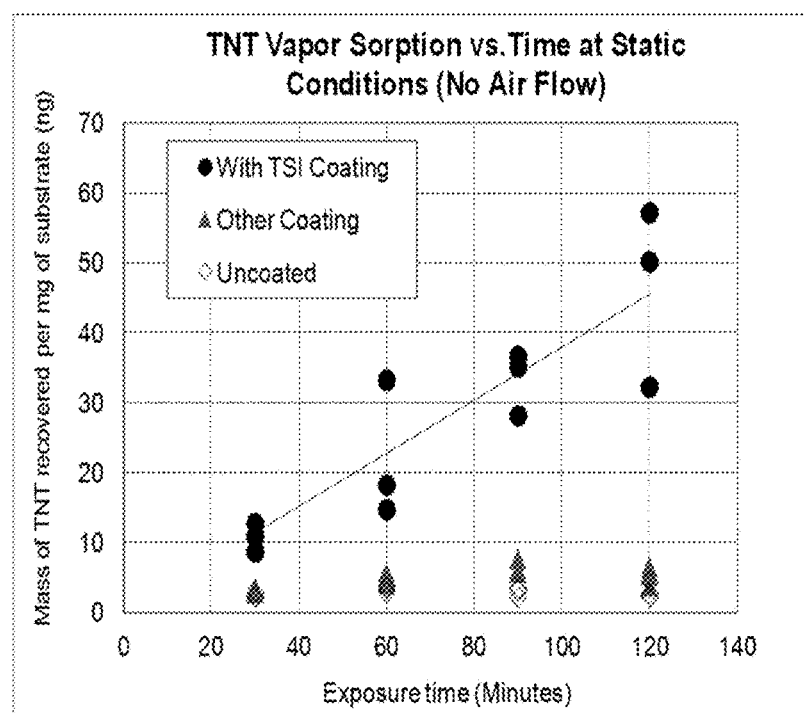
FIG. 9 shows with preconcentrator substrates with TSI coating, other coating and uncoated metal mesh were exposed to TNT vapors for 30, 60, 90 and 120 minutes without air circulation. TNT was extracted with a solvent and measured by GC/µECD.
Figure 10:
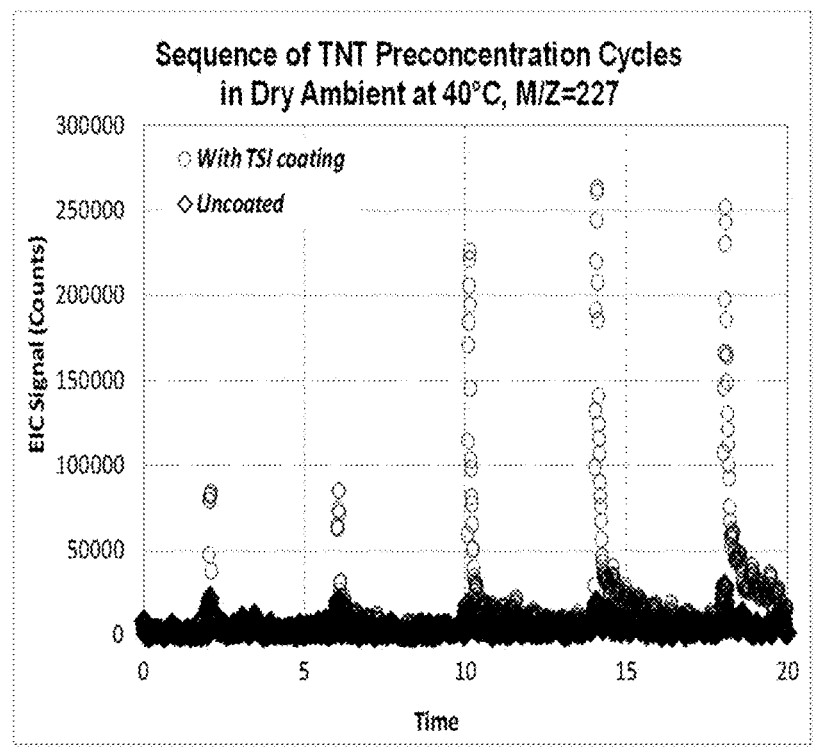
FIG. 10 shows sequence of TNT vapor preconcentration and pulsed vapor release. Preconcentrator coating shows no degradation after heating to 250° C. for a number of times (up to 25).

To measure quantitative preconcentration efficiency, the preconcentrator was interfaced with a quadruple mass spectrometer (MS). Experimental results (FIGS. 9 and 10) show repeatable TNT vapor pre-concentration. It should be noted that preconcentration efficiency will depend on the type of explosive and analyte vapor pressure.

Preconcentrator performance also was tested with COTS trace detector, QS-150, manufactured by Implant Sciences Corp. 0.5 g of DNT was placed into 50 ml syringe. Syringe pump was used to control sample air-flow and released vapors air-flow. Total time of vapor sampling and analysis for each set of experiment was 15 sec. Each curve on FIGS. 11-14 corresponds to 1 sec of sampling/analysis. All spectra are shown only for 29-40 ms region. Reactive ion peak (RIP) maximum amplitude was close to 3000 counts.

Figure 11:
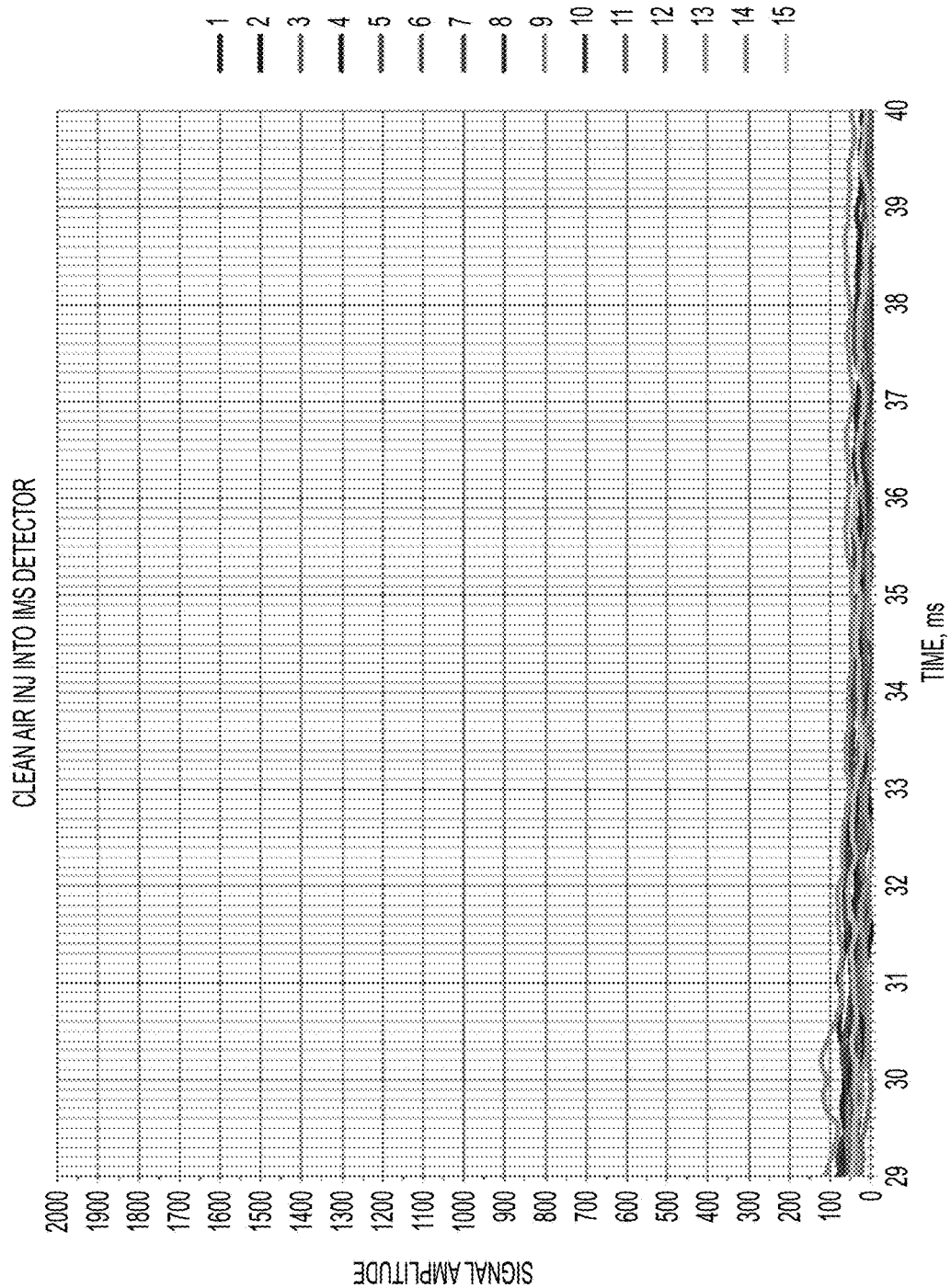
FIG. 11 IMS spectra of laboratory air according to an embodiment.
Figure 12:
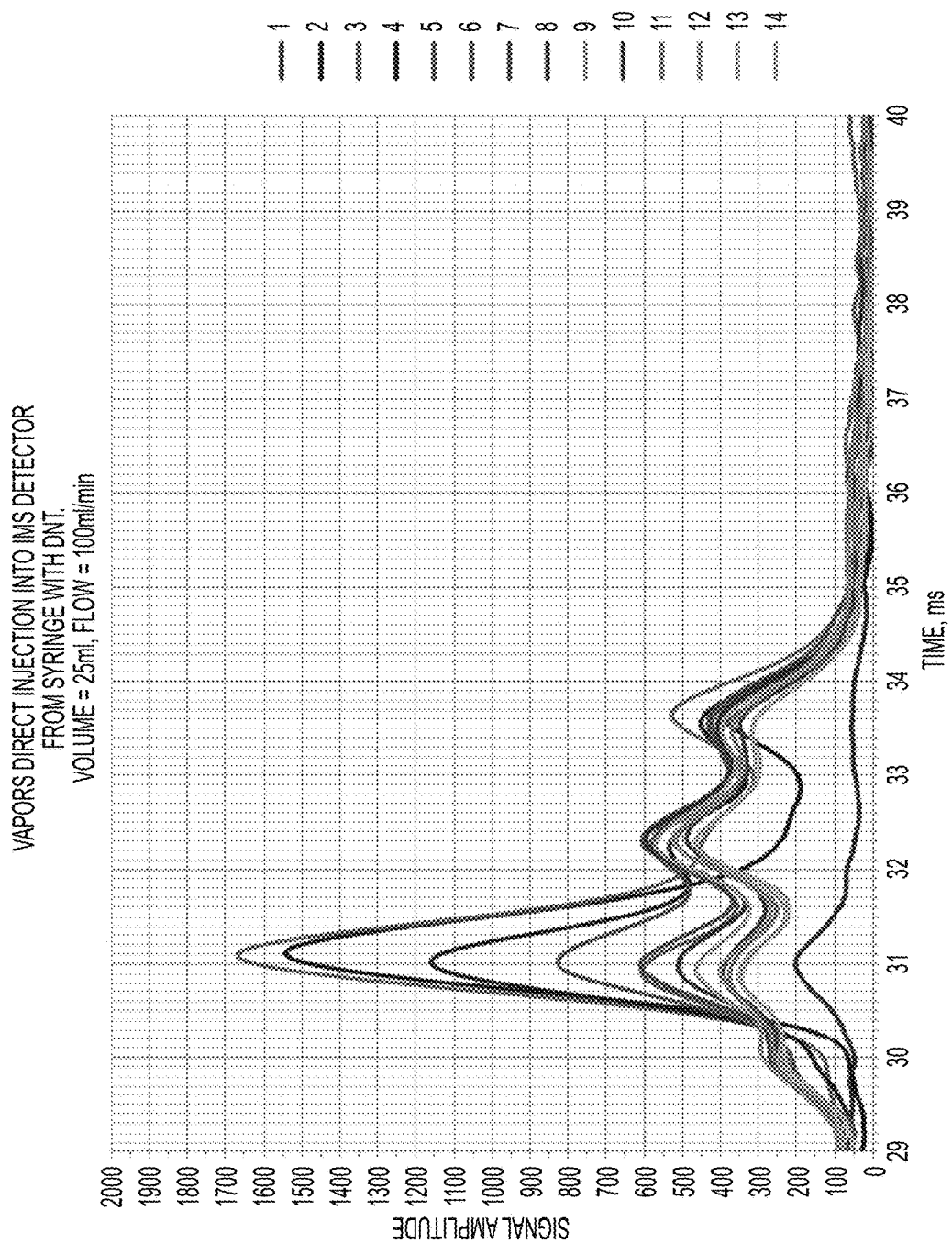
FIG. 12 shows IMS spectra of DNT vapors continuously injected into IMS detector from a syringe according to an embodiment. The showed spectra were taken with interval of 1 sec.
Figure 13:
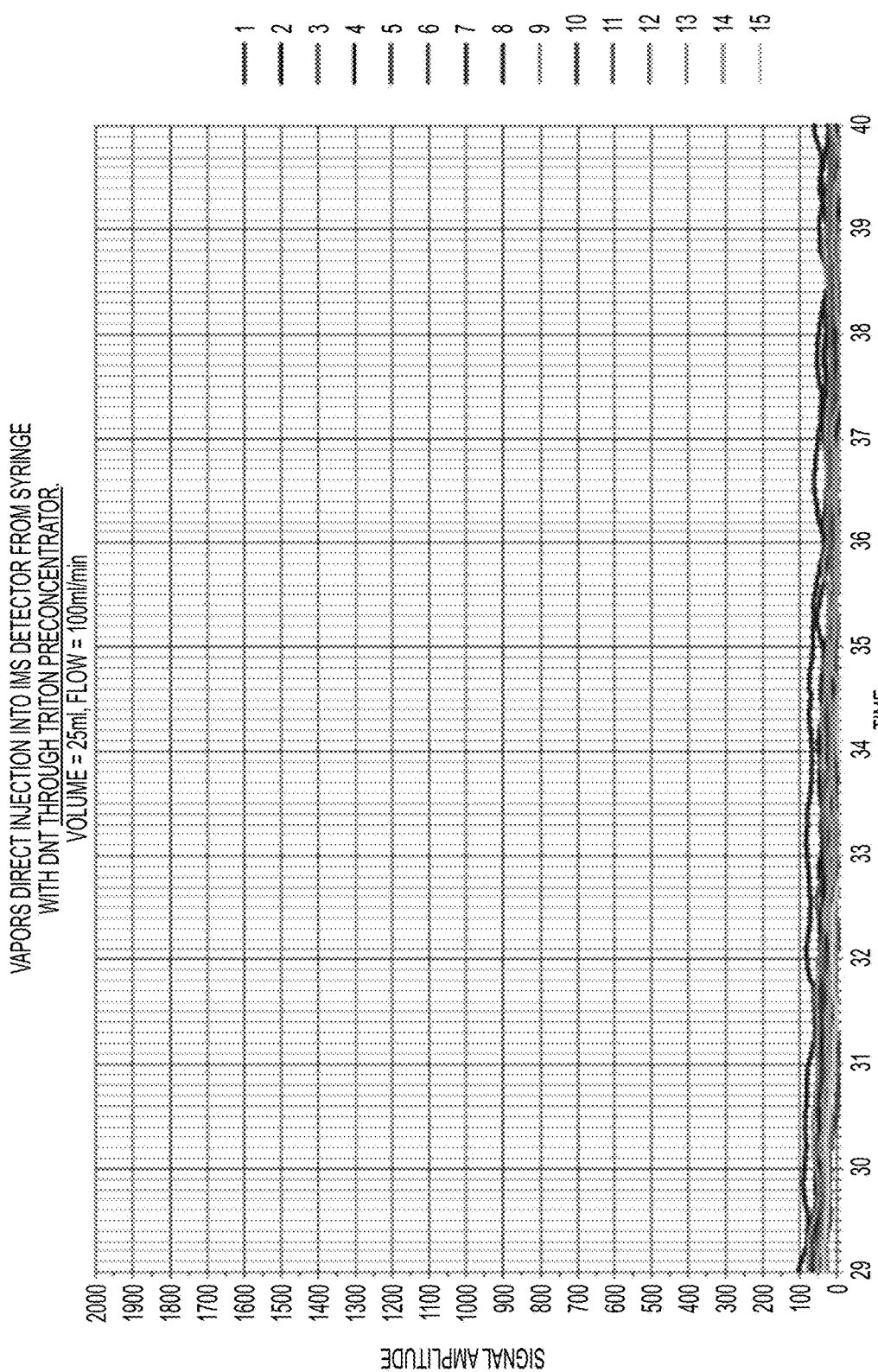
FIG. 13 shows IMS spectra of nitroglycerine vapors passed through the preconcentrator and injected into IMS detector.
Figure 14:
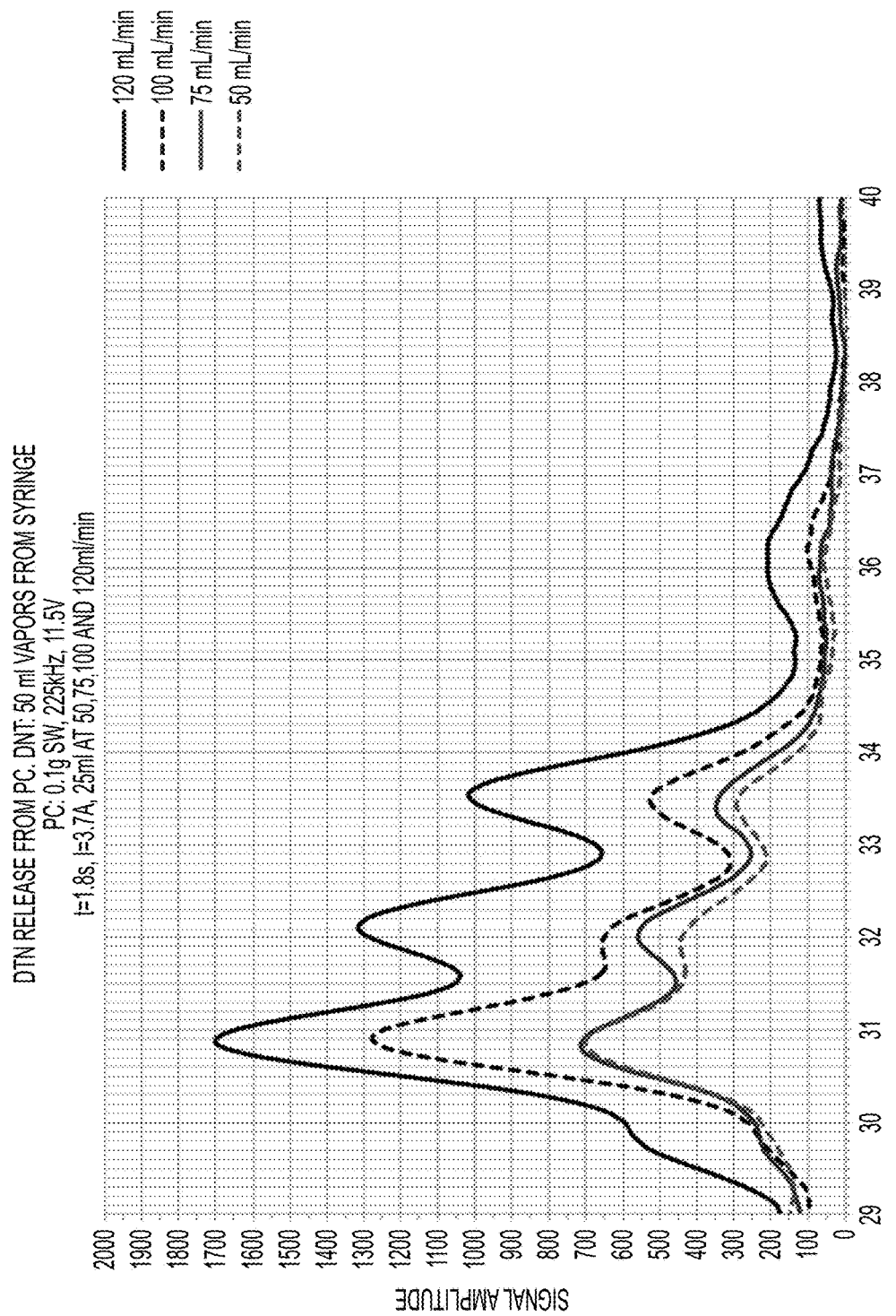
FIG. 14 shows IMS spectra of previously collected DNT vapor released within 1.8 sec of heating of preconcentrator with various release flow rates of 50, 75, 100 and 120 ml/min.

FIG. 11 shows IMS spectra of laboratory air. FIG. 12 shows IMS spectra related to DNT vapors injected from a syringe into ETD. The spectra were taken with interval of 1 sec. When preconcentrator was placed between the syringe with DNT vapors and IMS detector sampling port, DNT vapors could not reach the detector (see FIG. 13). After DNT vapor sampling the pre-concentrator with collected DNT vapors was heated within 1.8 sec and released vapors were injected into the detector. In a set of experiments we varied air-flow of released DNT vapors. FIG. 14 shows IMS detector response to released DNT vapors released with various flow rates of 50, 75, 100 and 120 ml/min.

What is claimed is:

1. A preconcentrator comprising:
a cartridge; and
a coated substrate having a resistivity of about $10^5$ ohm-meters ($\Omega \cdot m$) to about $10^{-7}$ $\Omega \cdot m$ and magnetic permeability of greater than about $1 \times 10^{-4}$ H/m enclosed within the cartridge;

and wherein the coated substrate comprises polymer having a backbone containing benzene, toluene, xylene, cyclohexane, dimethylcyclohexane, ethylcyclohexane, or combinations thereof.

2. The preconcentrator of claim 1, wherein the substrate is selected from the group consisting of metal fiber, woven metal fibers, non-woven metal fibers, porous metal, sheet metal, metal coated glass, metal coated plastic, metal coated ceramic, carbonaceous material, graphite, charcoal, activated carbon, activated carbon cloth, and combinations thereof.

3. The preconcentrator of claim 1, wherein the substrate relative permeability of greater than 100.

4. The preconcentrator of claim 1, wherein the substrate has an electrical resistivity of greater than $10^3$ $\Omega \cdot m$.

5. The preconcentrator of claim 1, wherein the cartridge further comprises at least a first reversibly sealable opening on one side of the cartridge and at least a second reversibly sealable opening on the opposite side of the cartridge.

6. A method for detecting a chemical comprising:
collecting particles and gases in a preconcentrator comprising a cartridge and a coated substrate enclosed in a cartridge, the substrate having a resistivity of about $10^5$ ohm-meters ($\Omega \cdot m$) to about $10^{-7}$ $\Omega \cdot m$ and magnetic permeability of greater than about $1 \times 10^{-4}$ H/m;
heating the substrate to release the particles and gases; and
detecting the chemical,
wherein the coated substrate comprises polymer having a backbone containing benzene, toluene, xylene, cyclohexane, dimethylcyclohexane, ethylcyclohexane, or combinations thereof.

7. The method of claim 6, wherein the substrate relative permeability of greater than 100.

8. The method of claim 6, wherein heating is carried out to about 200° C. to about 350° C.

9. The method of claim 6, wherein the heating is inductive heating.

10. The method of claim 9, wherein inductive heater is carried out at a frequency of about 100 kHz to about 10 MHz.

11. A sample collector comprising:
a preconcentrator comprising a coated substrate having a resistivity of about $10^5$ ohm-meters ($\Omega \cdot m$) to about $10^{-7}$ $\Omega \cdot m$ and magnetic permeability of greater than about $1 \times 10^{-4}$ H/m;
a sample collector housing having a preconcentrator holder sized to reversibly receive the preconcentrator; and
an air suction pump operably connected to the sample collector housing and configured to produce air flow through the preconcentrator,
wherein the coated substrate comprises polymer having a backbone containing benzene, toluene, xylene, cyclohexane, dimethylcyclohexane, ethylcyclohexane, or combinations thereof.

12. The sample collector of claim 11, further comprising a pulsed air nozzle connected to the sample collector housing.

13. The sample collector of claim 11, further comprising an air compressor operably connected to the sample collector housing and is configured to expel air from the pulsed air nozzle and direct the expelled air toward a sample collection area.

14. The sample collector of claim 11, wherein the air suction pump provides a flow of 1 m³/min to 10 m³/min.

15. A system comprising:
a sample collector comprising:
a preconcentrator comprising a coated substrate having a resistivity of about $10^5$ ohm-meters ($\Omega \cdot m$) to about $10^{-7}$ $\Omega \cdot m$ and magnetic permeability of greater than about $1 \times 10^{-4}$ H/m;
a sample collector housing having a preconcentrator holder sized to reversibly receive the preconcentrator;
a detector comprising:
a detector housing having a detector access port sized to reversibly receive the preconcentrator;
an induction heater contained within the detector housing, the induction heater configured to heat the preconcentrator; and
a sensing system connected to the access port and positioned to receive desorbed gases from the preconcentrator when the preconcentrator is received by the detector,
wherein the coated substrate comprises polymer having a backbone containing benzene, toluene, xylene, cyclohexane, dimethylcyclohexane, ethylcyclohexane, or combinations thereof.

16. The system of claim 15, further comprising an air suction pump operably connected to the sample collection housing and configured to produce air flow through the preconcentrator.

17. The system of claim 16, wherein the air suction pump provides a flow of 1 m³/min to 10 m³/min.

18. The system of claim 15, wherein the sample collector further comprises a pulsed air nozzle connected to the sample collector housing.

19. The system of claim 18, further comprising an air compressor operably connected to the sample collector housing and configured to expel air from the pulsed air nozzle and direct the expelled air toward a sample collection area.

20. The system of claim 15, wherein preconcentrator comprises a cartridge and a substrate having a resistivity of about $10^5$ ohm-meters ($\Omega \cdot m$) to about $10^{-7}$ $\Omega \cdot m$ enclosed within the cartridge.

21. The system of claim 15, wherein the detector comprises a temperature feedback that limits the temperature to about 200° C. to about 350° C.

22. The system of claim 15, wherein the detector further comprises a compressor operably connected to the detector access port and configured to generate a differential pressure across the preconcentrator when the preconcentrator is received by the detector.

23. The preconcentrator of claim 1, wherein the coated substrate comprises coating having polar functional groups selected from the group consisting of amide (—C(O)NH$_2$), C$_1$-C$_{10}$ alkyl amide, carboxylic acid (—COOH), C$_1$-C$_{10}$ alkyl carboxylic acid, hydroxyl (—OH), C$_1$-C$_{10}$ alkyl hydroxyl, C$_1$-C$_{10}$ alkyoxy, aldehyde (—C(O)H), C$_1$-C$_{10}$ alkyl aldehyde, ketone (—C(O)CH$_3$), C$_1$-C$_{10}$ alkyl ketone, amine (—NH$_2$), C$_1$-C$_{10}$ alkyl amine, epoxide, and carbonyl group.

24. The preconcentrator of claim 1, wherein the coated substrate comprises coating having non-polar functional groups selected from the group consisting of C$_1$-C$_{10}$ alkyl, C$_2$-C$_{10}$ alkene, C$_2$-C$_{10}$ alkyne, C$_6$-C$_{16}$ arene, halide (Br, F, Cl), C$_1$-C$_{10}$ alkyl halide, and cycloalkyl.

25. The preconcentrator of claim 1, wherein the coated substrate comprises coating that is a copolymer of 4-hydroxy[2.2]paracyclophane and 4-perfluoro-alkylcarbonly[2.2]paracyclophane.

26. The preconcentrator of claim 6, wherein the coated substrate comprises coating having polar functional groups selected from the group consisting of amide (—C(O)NH$_2$), C$_1$-C$_{10}$ alkyl amide, carboxylic acid (—COOH), C$_1$-C$_{10}$ alkyl carboxylic acid, hydroxyl (—OH), C$_1$-C$_{10}$ alkyl hydroxyl, C$_1$-C$_{10}$ alkyoxy, aldehyde (—C(O)H), C$_1$-C$_{10}$ alkyl aldehyde, ketone (—C(O)CH$_3$), C$_1$-C$_{10}$ alkyl ketone, amine (—NH$_2$), C$_1$-C$_{10}$ alkyl amine, epoxide, and carbonyl group.

27. The preconcentrator of claim 6, wherein the coated substrate comprises coating having non-polar functional groups selected from the group consisting of C$_1$-C$_{10}$ alkyl, C$_2$-C$_{10}$ alkene, C$_2$-C$_{10}$ alkyne, C$_6$-C$_{16}$ arene, halide (Br, F, Cl), C$_1$-C$_{10}$ alkyl halide, and cycloalkyl.

28. The preconcentrator of claim 6, wherein the coated substrate comprises coating that is a copolymer of 4-hydroxy[2.2]paracyclophane and 4-perfluoro-alkylcarbonly [2.2]paracyclophane.

29. The preconcentrator of claim 11, wherein the coated substrate comprises coating having polar functional groups selected from the group consisting of amide (—C(O)NH$_2$), C$_1$-C$_{10}$ alkyl amide, carboxylic acid (—COOH), C$_1$-C$_{10}$ alkyl carboxylic acid, hydroxyl (—OH), C$_1$-C$_{10}$ alkyl hydroxyl, C$_1$-C$_{10}$ alkyoxy, aldehyde (—C(O)H), C$_1$-C$_{10}$ alkyl aldehyde, ketone (—C(O)CH$_3$), C$_1$-C$_{10}$ alkyl ketone, amine (—NH$_2$), C$_1$-C$_{10}$ alkyl amine, epoxide, and carbonyl group.

30. The preconcentrator of claim 11, wherein the coated substrate comprises coating having non-polar functional groups selected from the group consisting of C$_1$-C$_{10}$ alkyl, C$_2$-C$_{10}$ alkene, C$_2$-C$_{10}$ alkyne, C$_6$-C$_{16}$ arene, halide (Br, F, Cl), C$_1$-C$_{10}$ alkyl halide, and cycloalkyl.

31. The preconcentrator of claim 11, wherein the coated substrate comprises coating that is a copolymer of 4-hydroxy[2.2]paracyclophane and 4-perfluoro-alkylcarbonly [2.2]paracyclophane.

32. The preconcentrator of claim 15, wherein the coated substrate comprises coating having polar functional groups selected from the group consisting of amide (—C(O)NH$_2$), C$_1$-C$_{10}$ alkyl amide, carboxylic acid (—COOH), C$_1$-C$_{10}$ alkyl carboxylic acid, hydroxyl (—OH), C$_1$-C$_{10}$ alkyl hydroxyl, C$_1$-C$_{10}$ alkyoxy, aldehyde (—C(O)H), C$_1$-C$_{10}$ alkyl aldehyde, ketone (—C(O)CH$_3$), C$_1$-C$_{10}$ alkyl ketone, amine (—NH$_2$), C$_1$-C$_{10}$ alkyl amine, epoxide, and carbonyl group.

33. The preconcentrator of claim 15, wherein the coated substrate comprises coating having non-polar functional groups selected from the group consisting of C$_1$-C$_{10}$ alkyl, C$_2$-C$_{10}$ alkene, C$_2$-C$_{10}$ alkyne, C$_6$-C$_{16}$ arene, halide (Br, F, Cl), C$_1$-C$_{10}$ alkyl halide, and cycloalkyl.

34. The preconcentrator of claim 15, wherein the coated substrate comprises coating that is a copolymer of 4-hydroxy[2.2]paracyclophane and 4-perfluoro-alkylcarbonly [2.2]paracyclophane.

* * * * *